United States Patent [19]

Cascieri et al.

[11] Patent Number: 5,889,167
[45] Date of Patent: Mar. 30, 1999

[54] SYNTHETIC GLUCAGON BINDING PROTEINS

[75] Inventors: Margaret A. Cascieri, East Windsor; Gary A. Chicchi, East Brunswick; Michael P. Graziano, Scotch Plains; Patricia J. Hey, Fanwood, all of N.J.

[73] Assignee: Merck & Co., Inc., Rahway, N.J.

[21] Appl. No.: 859,873

[22] Filed: May 21, 1997

Related U.S. Application Data

[60] Provisional application No. 60/017,612 filed May 22, 1996.
[51] Int. Cl.$^6$ .............................. C12N 15/10; C12N 5/10; C07K 14/705
[52] U.S. Cl. .................. 536/23.1; 530/350; 536/23.5; 435/320.1; 435/325; 435/252.3; 435/254.11; 435/69.1
[58] Field of Search .................... 536/23.1, 23.5, 536/23.41; 530/350; 435/69.1, 320.1, 325, 252.3, 254.11

[56] References Cited

FOREIGN PATENT DOCUMENTS

WO95/04821  2/1995  WIPO .

OTHER PUBLICATIONS

Chicchi, et al., "Alterations in receptor activation and divalent cation activation of agonist binding . . . ", J. Biol. Chem., 21 Mar. 1997, vol. 272, No. 12 pp. 7765–7769.

Carruthers, et al., "Synthesis and expression of a gene for the rat glucgon receptor . . . ", J. Biol. Chem., 18 Nov. 1994, vol. 269, No. 46, pp. 29321–29328.

MacNiel, et al., "Cloning and expression of a human glucagon receptor.", Biochem. Biophys. Res. Comm., 14 Jan. 1994, vol. 198, No. 1, pp. 328–334.

Unson, et al., "Characterization of deletion and truncation mutants of the rat glucagon receptor.", J. Biol. Chem., 17 Nov. 1995, vol. 270, No. 46, pp. 27720–27727.

Tota, et al., "Interaction of [Flurescein–Trp25]glucagon with the human glucagon receptor expressed . . .", j. Biol. Chem., 3 Nov. 1995, vol. 270, No. 44, pp. 26466–26472.

Hamilton, et al., nursing 86 Drug Handbook, Pennsylvania, USA Springhouse Corporation 1986, pp. 494, col. 2 and p. 495, col. 1.

*Primary Examiner*—Lorraine Spector
*Assistant Examiner*—Claire M. Kaufman
*Attorney, Agent, or Firm*—Michael D. Yablonsky; Jack L. Tribble

[57] ABSTRACT

A synthetic human glucagon (hGlu) binding protein designated hGluΔ252–259 binding protein is cloned, expressed and used in an in vitro assay to screen for compounds that bind to the synthetic binding protein, including compounds that specifically stimulate or inhibit the binding of glucagon to the synthetic receptor. The invention includes the assay, the synthetic binding protein used in the assay, DNA encoding the synthetic binding protein, cells expressing the synthetic binding protein, and compounds identified through the use of the synthetic binding protein.

5 Claims, 3 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

| | | | |
|---|---|---|---|
| CTGTACCTGC | ACAACGAGAG | GAGCTTCTTC | 30 |

( 2 ) INFORMATION FOR SEQ ID NO:2:

( i ) SEQUENCE CHARACTERISTICS:
        ( A ) LENGTH: 1578 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
| AAGCTTTGCC | CCAGCTGTGC | AGCCCCTGCC | AGATGTGGGA | GGCAGCTAGC | TGCCCAGAGG | 60 |
| CATGCCCCCC | TGCCAGCCAC | AGCGACCCCT | GCTGCTGTTG | CTGCTGCTGC | TGGCCTGCCA | 120 |
| GCCACAGGTC | CCCTCCGCTC | AGGTGATGGA | CTTCCTGTTT | GAGAAGTGGA | AGCTCTACGG | 180 |
| TGACCAGTGT | CACCACAACC | TGAGCCTGCT | GCCCCCTCCC | ACGGAGCTGG | TGTGCAACAG | 240 |
| AACCTTCGAC | AAGTATTCCT | GCTGGCCGGA | CACCCCCGCC | AATACCACGG | CCAACATCTC | 300 |
| CTGCCCCTGG | TACCTGCCTT | GGCACCACAA | AGTGCAACAC | CGCTTCGTGT | TCAAGAGATG | 360 |
| CGGGCCCGAC | GGTCAGTGGG | TGCGTGGACC | CCGGGGGCAG | CCTTGGCGTG | ATGCCTCCCA | 420 |
| GTGCCAGATG | GATGGCGAGG | AGATTGAGGT | CCAGAAGGAG | GTGGCCAAGA | TGTACAGCAG | 480 |
| CTTCCAGGTG | ATGTACACAG | TGGGCTACAG | CCTGTCCCTG | GGGGCGCTGC | TCCTCGCCTT | 540 |
| GGCCATCCTG | GGGGGCCTCA | GCAAGCTGCA | CTGCACCCGC | AATGCCATCC | ACGCGAATCT | 600 |
| GTTTGCGTCC | TTCGTGCTGA | AAGCCAGCTC | CGTGCTGGTC | ATTGATGGGC | TGCTCAGGAC | 660 |
| CCGCTACAGC | CAGAAAATTG | GCGACGACCT | CAGTGTCAGC | ACCTGGCTCA | GTGATGGAGC | 720 |
| GGTGGCTGGC | TGCCGTGTGG | CCGCGGTGTT | CATGCAATAT | GGCATCGTGG | CCAACTACTG | 780 |
| CTGGCTGCTG | GTGGAGGGCC | TGTACCTGCA | CAACCTGCTG | GGCCTGGCCA | CCCTCCCCGA | 840 |
| GAGGAGCTTC | TTCAGCCTCT | ACCTGGGCAT | CGGCTGGGGT | GCCCCCATGC | TGTTCGTCGT | 900 |

```
CCCCTGGGCA   GTGGTCAAGT   GTCTGTTCGA   GAACGTCCAG   TGCTGGACCA   GCAATGACAA    960
CATGGGCTTC   TGGTGGATCC   TGCGGTTCCC   CGTCTTCCTG   GCCATCCTGA   TCAACTTCTT   1020
CATCTTCGTC   CGCATCGTTC   AGCTGCTCGT   GGCCAAGCTG   CGGGCACGGC   AGATGCACCA   1080
CACAGACTAC   AAGTTCCGGC   TGGCCAAGTC   CACGCTGACC   CTCATCCCTC   TGCTGGGCGT   1140
CCACGAAGTG   GTCTTCGCCT   TCGTGACGGA   CGAGCACGCC   CAGGGCACCC   TGCGCTCCGC   1200
CAAGCTCTTC   TTCGACCTCT   TCCTCAGCTC   CTTCCAGGGC   CTGCTGGTGG   CTGTCCTCTA   1260
CTGCTTCCTC   AACAAGGAGG   TGCAGTCGGA   GCTGCGGCGG   CGTTGGCACC   GCTGGCGCCT   1320
GGGCAAAGTG   CTATGGGAGG   AGCGGAACAC   CAGCAACCAC   AGGGCCTCAT   CTTCGCCCGG   1380
CCACGGCCCT   CCCAGCAAGG   AGCTGCAGTT   TGGGAGGGGT   GGTGGCAGCC   AGGATTCATC   1440
TGCGGAGACC   CCCTTGGCTG   GTGGCCTCCC   TAGATTGGCT   GAGAGCCCCT   TCTGAACCCT   1500
GCTGGGACCC   CAGCTAGGGC   TGGACTCTGG   CACCCAGAGG   GCGTCGCTGG   ACAACCCAGA   1560
ACTGGACGCC   CATCTAGA                                                        1578
```

(2) INFORMATION FOR SEQ ID NO:3:

(i) SEQUENCE CHARACTERISTICS:
　　　　(A) LENGTH: 477 amino acids
　　　　(B) TYPE: amino acid
　　　　(C) STRANDEDNESS: single
　　　　(D) TOPOLOGY: linear (ii) MOLECULE TYPE: protein (xi) SEQUENCE DESCRIPTION: SEQ ID NO:3:

```
Met  Pro  Pro  Cys  Gln  Pro  Gln  Arg  Pro  Leu  Leu  Leu  Leu  Leu  Leu  Leu
 1                   5                        10                       15

Leu  Ala  Cys  Gln  Pro  Gln  Val  Pro  Ser  Ala  Gln  Val  Met  Asp  Phe  Leu
                20                  25                       30

Phe  Glu  Lys  Trp  Lys  Leu  Tyr  Gly  Asp  Gln  Cys  His  His  Asn  Leu  Ser
           35                       40                       45

Leu  Leu  Pro  Pro  Pro  Thr  Glu  Leu  Val  Cys  Asn  Arg  Thr  Phe  Asp  Lys
      50                       55                       60

Tyr  Ser  Cys  Trp  Pro  Asp  Thr  Pro  Ala  Asn  Thr  Thr  Ala  Asn  Ile  Ser
65                        70                       75                       80

Cys  Pro  Trp  Tyr  Leu  Pro  Trp  His  His  Lys  Val  Gln  His  Arg  Phe  Val
                     85                       90                       95

Phe  Lys  Arg  Cys  Gly  Pro  Asp  Gly  Gln  Trp  Val  Arg  Gly  Pro  Arg  Gly
               100                      105                      110

Gln  Pro  Trp  Arg  Asp  Ala  Ser  Gln  Cys  Gln  Met  Asp  Gly  Glu  Glu  Ile
          115                      120                      125

Glu  Val  Gln  Lys  Glu  Val  Ala  Lys  Met  Tyr  Ser  Ser  Phe  Gln  Val  Met
     130                      135                      140

Tyr  Thr  Val  Gly  Tyr  Ser  Leu  Ser  Leu  Gly  Ala  Leu  Leu  Leu  Ala  Leu
145                      150                      155                      160

Ala  Ile  Leu  Gly  Gly  Leu  Ser  Lys  Leu  His  Cys  Thr  Arg  Asn  Ala  Ile
                    165                      170                      175

His  Ala  Asn  Leu  Phe  Ala  Ser  Phe  Val  Leu  Lys  Ala  Ser  Ser  Val  Leu
               180                      185                      190

Val  Ile  Asp  Gly  Leu  Leu  Arg  Thr  Arg  Tyr  Ser  Gln  Lys  Ile  Gly  Asp
          195                      200                      205

Asp  Leu  Ser  Val  Ser  Thr  Trp  Leu  Ser  Asp  Gly  Ala  Val  Ala  Gly  Cys
     210                      215                      220

Arg  Val  Ala  Ala  Val  Phe  Met  Gln  Tyr  Gly  Ile  Val  Ala  Asn  Tyr  Cys
```

|     |     |     |     |     |     |     |     |     |     |     |     |     |     |     |
| --- | --- | --- | --- | --- | --- | --- | --- | --- | --- | --- | --- | --- | --- | --- |
| 225 |     |     |     |     | 230 |     |     |     | 235 |     |     |     | 240 |     |
| Trp | Leu | Leu | Val | Glu 245 | Gly | Leu | Tyr | Leu | His 250 | Asn | Leu | Leu | Gly 255 | Leu | Ala |
| Thr | Leu | Pro | Glu 260 | Arg | Ser | Phe | Phe | Ser 265 | Leu | Tyr | Leu | Gly | Ile 270 | Gly | Trp |
| Gly | Ala | Pro 275 | Met | Leu | Phe | Val | Val 280 | Pro | Trp | Ala | Val | Val 285 | Lys | Cys | Leu |
| Phe | Glu 290 | Asn | Val | Gln | Cys | Trp 295 | Thr | Ser | Asn | Asp | Asn 300 | Met | Gly | Phe | Trp |
| Trp 305 | Ile | Leu | Arg | Phe | Pro 310 | Val | Phe | Leu | Ala | Ile 315 | Leu | Ile | Asn | Phe | Phe 320 |
| Ile | Phe | Val | Arg | Ile 325 | Val | Gln | Leu | Leu | Val 330 | Ala | Lys | Leu | Arg | Ala 335 | Arg |
| Gln | Met | His | His 340 | Thr | Asp | Tyr | Lys | Phe 345 | Arg | Leu | Ala | Lys | Ser 350 | Thr | Leu |
| Thr | Leu | Ile 355 | Pro | Leu | Leu | Gly | Val 360 | His | Glu | Val | Val | Phe 365 | Ala | Phe | Val |
| Thr | Asp 370 | Glu | His | Ala | Gln | Gly 375 | Thr | Leu | Arg | Ser | Ala 380 | Lys | Leu | Phe | Phe |
| Asp 385 | Leu | Phe | Leu | Ser | Ser 390 | Phe | Gln | Gly | Leu | Leu 395 | Val | Ala | Val | Leu | Tyr 400 |
| Cys | Phe | Leu | Asn | Lys 405 | Glu | Val | Gln | Ser | Glu 410 | Leu | Arg | Arg | Arg | Trp 415 | His |
| Arg | Trp | Arg | Leu 420 | Gly | Lys | Val | Leu | Trp 425 | Glu | Glu | Arg | Asn | Thr 430 | Ser | Asn |
| His | Arg | Ala 435 | Ser | Ser | Ser | Pro | Gly 440 | His | Gly | Pro | Pro | Ser 445 | Lys | Glu | Leu |
| Gln | Phe 450 | Gly | Arg | Gly | Gly | Gly 455 | Ser | Gln | Asp | Ser | Ser 460 | Ala | Glu | Thr | Pro |
| Leu 465 | Ala | Gly | Gly | Leu | Pro 470 | Arg | Leu | Ala | Glu | Ser 475 | Pro | Phe |

SYNTHETIC GLUCAGON BINDING PROTEINS

The present application is entitled to the benefits of U.S. provisional application Ser. No. 60/017,612, filed on May 22, 1996.

BACKGROUND OF THE INVENTION

Glucagon is a major counterregulatory hormone that attenuates the inhibition of liver glucogenesis by insulin. Glucagon receptors are found primarily in liver, although their presence has been documented in kidney and adipose tissue. Type II diabetics have elevated levels of plasma glucagon and increased rates of hepatic glucose production. In fact, the rate of hepatic glucose production positively correlates with fasting blood glucose levels in type II diabetes. Therefore, antagonists of glucagon have the potential to improve insulin responsiveness in the liver, decrease the rate of gluconeogenesis and lower the rate of hepatic glucose output resulting in a decrease in the levels of plasma glucose.

Glucagon action is mediated by a G protein-coupled receptor that stimulates cyclic AMP accumulation via activation of Gs. G-protein coupled receptors are characterized by the ability of agonists to promote the formation of a high affinity ternary complex between the agonist, the receptor and the G-protein. The α subunit of the G-protein contains a guanine nucleotide binding site that, in the high affinity ternary [G protein-receptor-agonist] complex, is occupied by GDP. In the presence of physiological concentrations of GTP, the GDP molecule in the guanine nucleotide binding site of the G protein is displaced by a GTP molecule. The binding of GTP dissociates the α subunit of the G protein from its β and γ subunits and from the receptor, thereby activating the G-protein to stimulate downstream effectors (adenylyl cyclase in the case of the glucagon receptor) and propagating the intracellular signal. Thus, the ternary complex is transient in the presence of physiological concentrations of GTP. Because the affinity of the agonist for the receptor-G protein complex is higher than its affinity for the uncomplexed receptor, one consequence of the destabilization of the ternary complex is a reduction in the affinity of the receptor for the agonist. Thus, the affinity of agonists for G-protein coupled receptors is a function of the efficiency with which the receptor is coupled to the G-protein. In contrast, antagonists bind with the same affinity to the receptor in the presence or absence of G-protein coupling.

G protein-coupled receptors such as the glucagon receptor are predicted to have seven transmembrane domains linked by hydrophilic loops. Extensive modeling and mutagenesis experiments show that the binding domain for small molecules is within the transmembrane helical domains, although peptide agonist binding also involves the hydrophilic extracellular domains. However, the intracellular loop domains are involved in coupling of receptor to G-proteins. Deletion of either the amino terminal or carboxyl terminal sections of the third intracellular loop led to loss of functional coupling of the β-adrenergic receptor to Gs. However, these altered receptors maintained high affinity for agonist. The amino acids of the intracellular portions of the Glucagon receptor are shown as follows: loop 1, positions 167–173; loop 2; positions 250–262, loop 3, positions 332–349; and the carboxyl end, positions 404–477; of SEQ ID NO:3. Subsequent amino acid replacements in the third intracellular loop confirmed the role of this region in G protein interaction.

A human glucagon receptor has been cloned and expressed (D. MacNeil et al., 1994, Bioch. Biophys. Res. Comm. 198:328–334). We have characterized a mutant of the human glucagon receptor in which residues 252 to 259 in the second intracellular loop are deleted. The mutant protein is designated hGluΔ252–259 binding protein. When hGluΔ252–259 binding protein is expressed in COS cells, glucagon does not stimulate cAMP accumulation, suggesting that the hGluΔ252–259 binding protein does not couple to Gs upon agonist binding. However, the hGluΔ252–259 binding protein has higher affinity for glucagon than the wild type receptor, suggesting that the mutation locks the hGluΔ252–259 binding protein into a conformation with high affinity for agonist. Thus, hGluΔ252–259 binding protein is a high affinity glucagon binding protein that does not function as a glucagon receptor (ie., it does not transduce a signal).

SUMMARY OF THE INVENTION

A synthetic human glucagon (hGlu) binding protein lacking amino acid residues 252 through 259 of the wild type human glucagon receptor (hGluΔ252–259 binding protein) is cloned, expressed and used in an in vitro assay to screen for compounds that bind to the synthetic binding protein, including compounds that specifically stimulate or inhibit the high affinity binding of glucagon to the synthetic binding protein. The invention includes the assay, the synthetic binding protein used in the assay, DNA encoding the synthetic binding protein, cells expressing the synthetic binding protein, and compounds identified through the use of the synthetic binding protein.

DETAILED DESCRIPTION OF THE INVENTION

Figure 1:
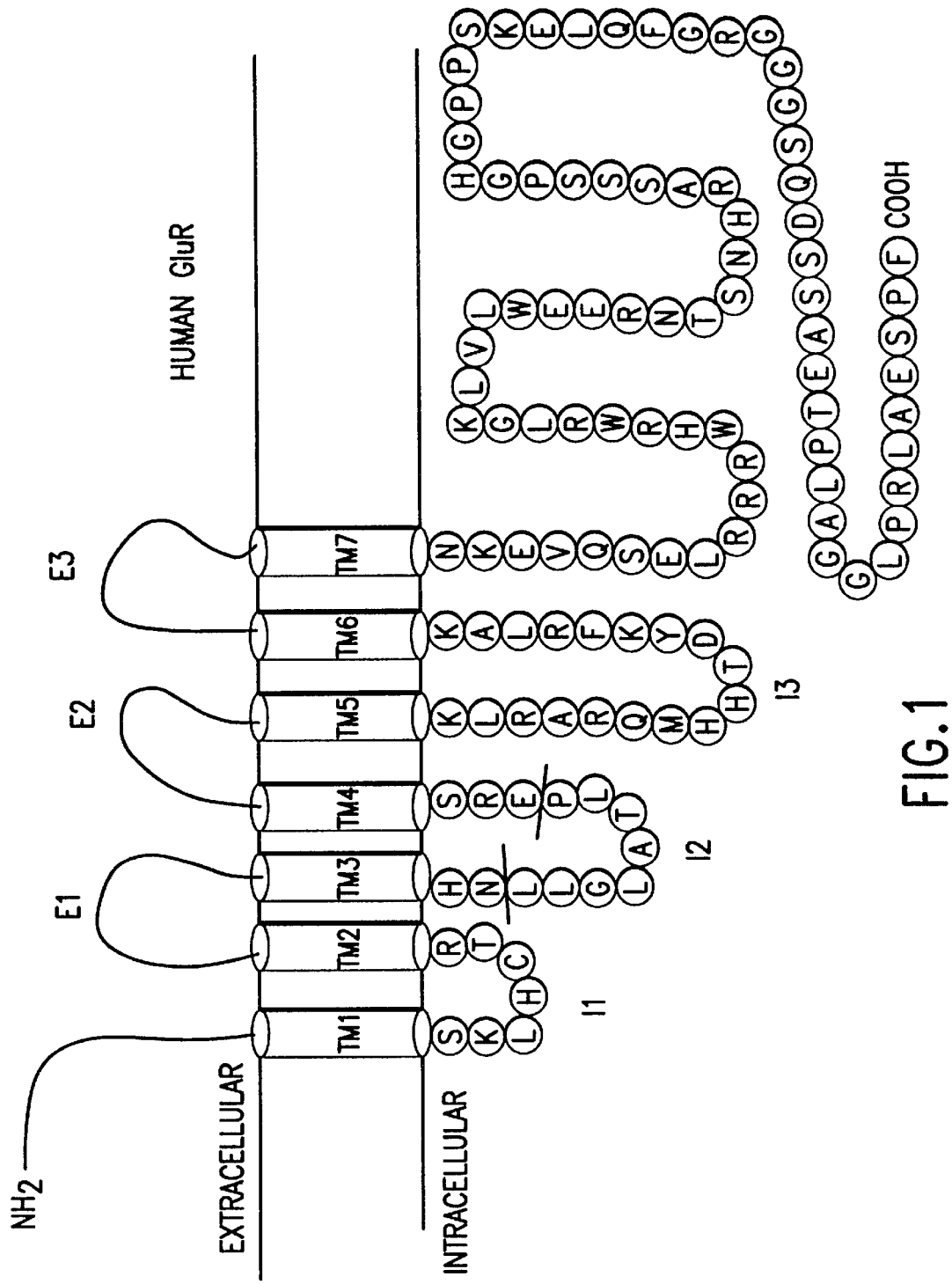
FIG. 1 shows the sequence of the intracellular domains of the human glucagon receptor and the position of the deletion in intracellular loop 2 (SEQ. ID. NO.:3).
Figure 2:
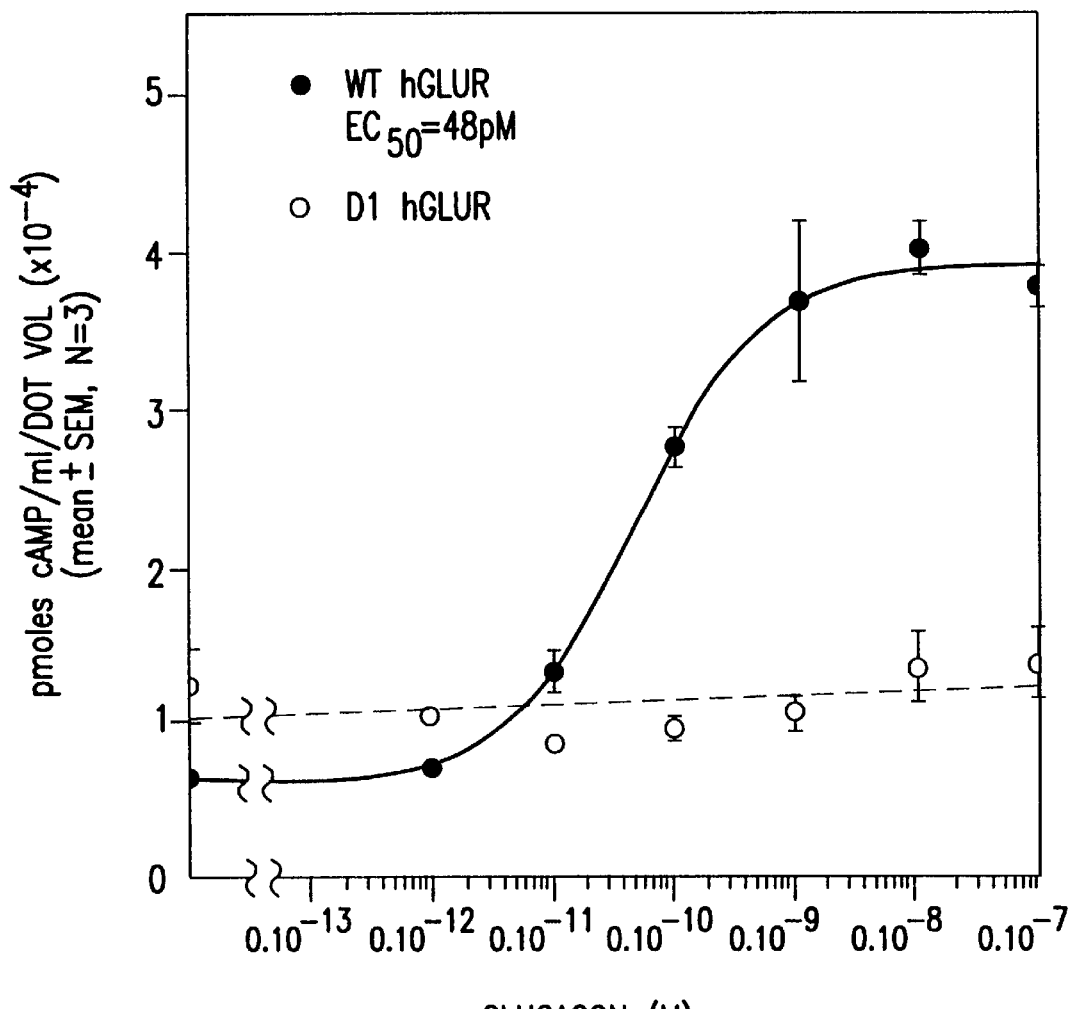
FIG. 2 shows the effect of glucagon on cAMP synthesis in COS cells transiently expressing either the wild type glucagon receptor or the hGluΔ252–259 binding protein.
Figure 3:
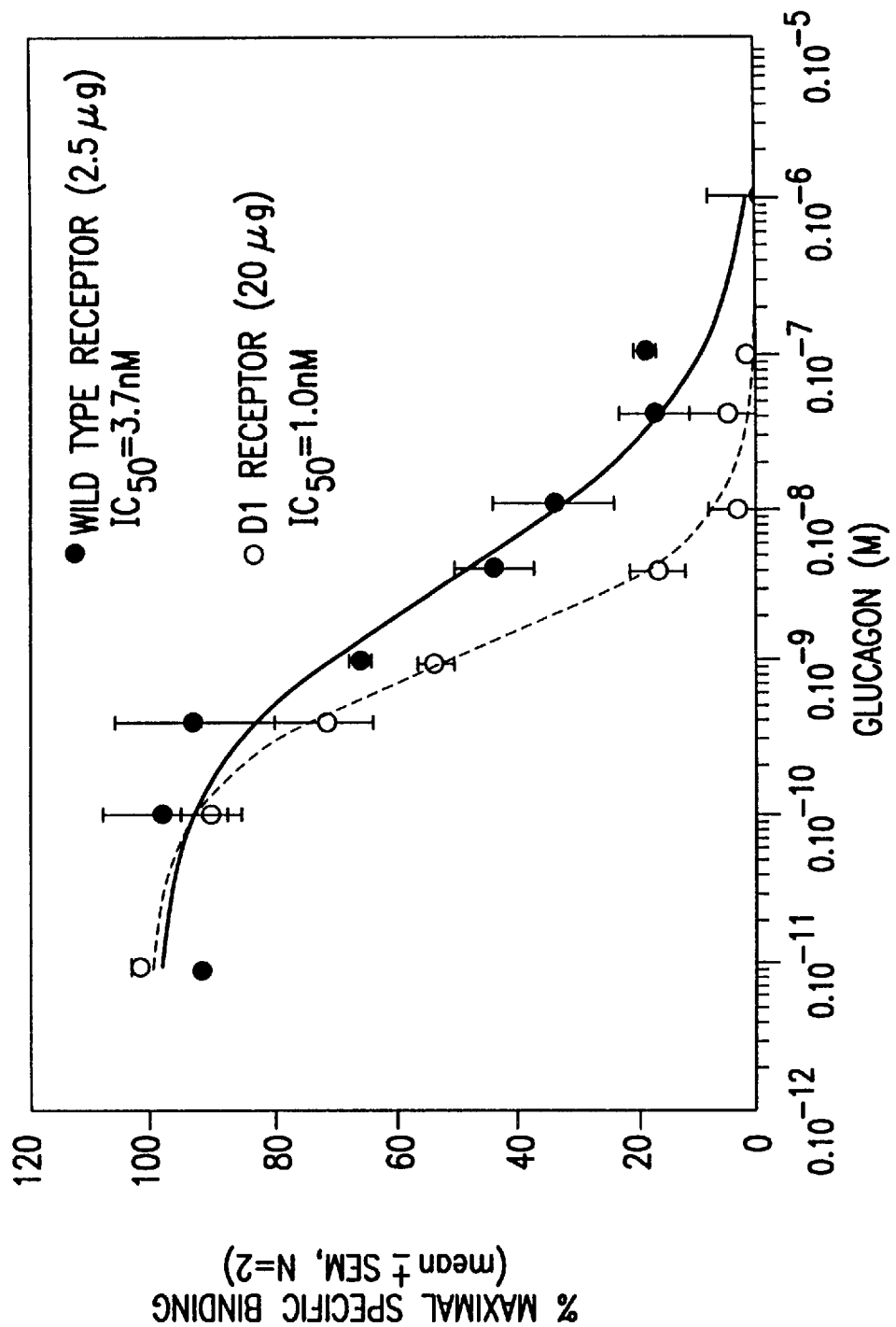
FIG. 3 shows $^{125}$I-glucagon binding to membranes from COS cells transiently expressing wild type glucagon receptor or the hGluΔ252–259 binding protein.

A synthetic human glucagon (hGlu) binding protein lacking amino acid residues 252 through 259 of the wild type human glucagon receptor (hGluΔ252–259 binding protein) is cloned, expressed and used in an in vitro assay to screen for compounds that bind to the synthetic binding protein, including compounds that specifically stimulate or inhibit the high affinity binding of glucagon to the synthetic binding protein. The invention includes the assay, the synthetic binding protein used in the assay, DNA encoding the synthetic binding protein, cells expressing the synthetic binding protein, and compounds identified through the use of the synthetic binding protein.

The human glucagon receptor (hGlu) was identified, cloned and expressed in cell cultures by the instant inventors.

Once the human glucagon receptor or hGluΔ252–259 binding protein is cloned and expressed in a non-human cell line, such as COS-7 cells or CHO cells, the recombinant proteins are free of other human proteins. The membranes from the recombinant cells expressing these proteins are then isolated according to methods known in the art and may be used in a variety of membrane associated binding assays. One example of such an assay is described by Wright and Rodbell (J. Biol. Chem. 254:268–269, 1979). Generally, a compound of interest is used to compete with the binding of a known, quantifiable glucagon receptor ligand. By increasing the amount of unlabeled test compound, the labeled compound is competed off the receptor or hGluΔ252–259 binding protein. From these experiments, an $IC_{50}$ value for each test compound is determined.

Thus, according to this invention, a method is provided for identifying compounds that bind synthetic hGluΔ252–259 binding protein comprising the following steps:

(a) cloning the synthetic hGluΔ252–259 binding protein;

(b) splicing the cloned hGluΔ252–259 binding protein into an expression vector to produce a construct such that the hGluΔ252–259 binding protein is operably linked to transcription and translation signals sufficient to induce expression of the binding protein upon introduction of the construct into a prokaryotic or eukaryotic cell;

(c) introducing the construct into a prokaryotic or eukaryotic cell that does not express a glucagon receptor or binding protein in the absence of the introduced construct; and (d) incubating cells or membranes isolated from cells produced in step (c) with a quantifiable compound known to bind to human glucagon receptors, and subsequently adding test compounds at a range of concentrations so as to compete the quantifiable compound from the receptor, such that an $IC_{50}$ for the test compound is obtained as the concentration of test compound at which 50% of the quantifiable compound becomes displaced from the receptor or binding protein.

Whereas glucagon has been shown to counter the inhibitory effect of insulin on liver glucogenesis, an antagonist of glucagon action discovered as described above would increase insulin sensitivity and would be useful in the treatment of diabetes.

The following examples are provided to further define the invention without, however, limiting the invention to the particulars of these examples.

EXAMPLE 1

Mutagenesis of a cloned human glucagon receptor was performed using the Bio-Rad Mutagene Phagemid In Vitro mutagenesis kit, version 2. The sequence of the wild type receptor was modified to produce the hGluΔ252–259 binding protein using the oligonucleotide primer 5' CTG TAC CTG CAC AAC GAG AGG AGC TTC TTC 3' (SEQ ID NO:1). This primer sequence corresponds to nucleotides 739 through 753 and 778 through 792 of the coding sequence of the human glucagon receptor. The deletion (ie., nucleotides 754 through 777 of the coding sequence of the human glucagon receptor) was confirmed by sequencing. The cDNA was ligated into the vector PCI/neo for expression studies.

COS cells were transfected in T175 flask monolayers using 10 μg cDNA and 8 mg DEAE-dextran in Dulbecco's modified Eagles medium containing 10% Nuserum and 100 μM chloroquine for two hours at 37° C. in 5% $CO_2$ incubation followed by two minute shock in 10% DMSO. Cells were maintained in fresh growth medium overnight then were harvested and seeded into T175 flasks for binding and 24-well dishes for cyclase activity measurement. After two days, cells were harvested from flasks using enzyme-free dissociation fluid, homogenized and the crude membrane pellet was recovered by centrifugation. $^{125}$I-glucagon (58 pM) binding to the membrane preparation was measured in 20 mM Tris pH 7.4 containing 2.5 mM $MgCl_2$, 1 mM DTT, 5 μg/ml leupeptin, 10 μg/ml benzamidine, 40 μg/ml bacitracin, 5 μg/ml soybean trypsin inhibitor and 3 μM o-phenanthroline ±1 μM glucagon for 1 hour. Bound cpm were recovered by filtration using aTomtec harvester and quantitfied in a gamma-scintillation counter. Functional responses in transfectants were measured by exposing the cell monolayers to Dulbecco's modified Eagles medium (basal), DMEM with increasing concentrations of glucagon or DMEM with 10 μM forskolin for thirty minutes at 22° C. in order to generate intracellular cAMP. Cells were lysed in HCl and cAMP in lysates was acetylated and quantitated by radioimmunoassay.

The amount of receptor protein in COS membranes was normalized by quantitating the binding of an antibody to the C-terminus of the glucagon receptor to a dot blot using various concentrations of membrane protein.

EXAMPLE 2

The sequence of the intracellular domains of the human glucagon receptor and the position of the deletion (Δ252–259) in intracellular loop 2 are shown in FIG. 1. Expression of the wild type human glucagon receptor in COS cells produced an 8-fold increase in intracellular cAMP levels upon addition of glucagon (FIG. 2). The $EC_{50}$ for glucagon activation is 48 pM. In contrast, virtually no increase in cAMP levels is observed in cells expressing the hGluΔ252–259 binding protein at up to 100 nM glucagon (FIG. 2). These data were normalized for differences in expression levels of the two proteins as described below. These data suggest that the deletion of residues 252 to 259 in intracellular loop two of the human glucagon receptor disrupts the binding interaction between the receptor and Gs.

Quantitation of the amount of human glucagon receptor or hGluΔ252–259 binding protein expressed in COS membranes was performed utilizing an antibody to the carboxyl terminal of the glucagon receptor. These experiments show that there is 38% higher expression of the wild type glucagon receptor than the hGluΔ252–259 binding protein in the transfection experiment shown in FIG. 2.

Inhibition of the binding of $^{125}$I-glucagon to the wild type human glucagon receptor and hGluΔ252–259 binding protein by unlabeled glucagon shows that glucagon has a 4-fold higher affinity for the hGluΔ252–259 binding protein than for the wild type human glucagon receptor (FIG. 3). Thus, despite the lack of coupling to Gs, the hGluΔ252–259 binding protein has high affinity for glucagon. Scatchard analysis of these data show that the binding of glucagon to the hGluΔ252–259 binding protein is fit to a single site with a Kd for glucagon of 0.7 nM. These data suggest that the deletion of residues 252 to 259 locks the protein into a conformation that has high affinity for agonist.

EXAMPLE 3

Compounds that bind synthetic hGluΔ252–259 binding protein are identified by a method such as:

(a) cloning the synthetic hGluΔ252–259 binding protein;

(b) splicing the cloned hGluΔ252–259 binding protein into an expression vector to produce a construct such that the hGluΔ252–259 binding protein is operably linked to transcription and translation signals sufficient to induce expression of the binding protein upon introduction of the construct into a prokaryotic or eukaryotic cell;

(c) introducing the construct into a prokaryotic or eukaryotic cell that does not express a glucagon receptor or binding protein in the absence of the introduced construct; and (d) incubating cells or membranes isolated from cells produced in step (c) with a quantifiable compound known to bind to human glucagon receptors, and subsequently adding test compounds at a range of concentrations so as to compete the quantifiable compound from the receptor, such that an $IC_{50}$ for the test compound is obtained as the concentration of test compound at which 50% of the quantifiable compound becomes displaced from the receptor or binding protein.

EXAMPLE 4

Compounds identified by the method of Example 3 are formulated into pharmaceutical compositions.

---

What is claimed:

1. A recombinant nucleic acid molecule comprising a nucleotide sequence encoding a human glucagon binding protein wherein the amino acid sequence of the protein is derived from a wild-type human glucagon receptor by deletion of the amino acids of the second intracellular loop corresponding to amino acids 252–259 of SEQ.ID.NO.:3.

2. The nucleic acid molecule of claim 1, wherein the nucleotide sequence encoding the binding protein is operably linked to regulatory sequences that direct the expression of the binding protein in a host cell.

3. A recombinant host cell comprising the nucleic acid of claim 1.

4. A recombinant human glucagon binding protein, wherein the amino acid sequence of the protein is derived from a wild-type human glucagon receptor by deletion of the amino acids of the second intracellular loop corresponding to amino acids 252–259 of SEQ.ID.NO.:3 are deleted.

5. The protein of claim 4 having the amino acid sequence set forth in SEQ.ID.NO.:3 wherein amino acids 252–259 are deleted.

* * * * *